United States Patent [19]

Maruyama et al.

[11] 3,954,756

[45] May 4, 1976

[54] METHOD FOR PRODUCING PYRIMIDINE

[75] Inventors: Tetsuo Maruyama; Iwao Mikami; Kazuo Imaoka, all of Osaka, Japan

[73] Assignee: Takeda Chemical Industries, Ltd., Osaka, Japan

[22] Filed: May 10, 1973

[21] Appl. No.: 358,965

[30] Foreign Application Priority Data
May 12, 1972 Japan............................ 47-47412

[52] U.S. Cl............................ 260/256.4 N; 260/463; 260/465 D; 260/465.4
[51] Int. Cl.²........................................ C07D 239/00
[58] Field of Search............... 260/256.4 R, 256.4 N

[56] References Cited
UNITED STATES PATENTS

| | | | |
|---|---|---|---|
| 2,602,794 | 7/1952 | Hitchings et al............. | 260/256.4 N |
| 2,658,897 | 11/1953 | Hitchings et al............. | 260/256.4 N |
| 2,820,050 | 1/1958 | Hultquist........................ | 260/465 D |
| 3,036,075 | 5/1962 | Kaiser............................ | 260/256.4 N |
| 3,211,778 | 10/1965 | Kollonitsch................... | 260/256.4 N |
| 3,830,812 | 8/1974 | Ramsey......................... | 260/256.4 N |

OTHER PUBLICATIONS

Brown, "Heterocyclic Compounds–The Pyrimidines," 1962, pp. 61–62.

*Primary Examiner*—Joseph P. Brust
*Attorney, Agent, or Firm*—Burgess Ryan and Wayne

[57] ABSTRACT

2-Alkyl-4-amino-5-formylaminomethylpyrimidine is produced in a higher yield and using less process steps than the known methods by subjecting β-aminopropionitrile to formylation in the presence of metal alcoholate, subjecting the resulting metal salt of α-formyl-β-formylaminopropionitrile to alkylation or acylation, followed by allowing the thus produced α-alkoxy (or acyloxy)-methylene-β-formylaminopropionitrile to react with an amidine.

8 Claims, No Drawings

METHOD FOR PRODUCING PYRIMIDINE

This invention relates to a novel process for the production of a 2-alkyl-4-amino-5-formylaminomethylpyrimidine which is useful as an intermediate for the synthesis of Vitamin $B_1$ or its analogues.

Heretofore, many methods for producing the pyrimidine portion of thiamine have been known.

For example, β-ethoxypropionitrile is subjected to formylation in the presence of sodium alcoholate, subjecting the resulting α-sodioformyl-β-ethoxypropionitrile to methylation, allowing the thus produced α-methoxymethyleneβ-ethoxypropionitrile to react with acetamidine to give 2-methyl-4-amino-5-ethoxymethylpyrimidine or 2-methyl-4-amino-5-acetylaminomethylpyrimidine, and subjecting the former to bromination, followed by amination, or subjecting the latter to deacetylation, whereby 2-methyl-4-amino-5-aminomethylpyrimidine is prepared. However, those processes give the products in low yields.

It has also been known that a 2-alkyl-4-amino-5-formylaminomethylpyrimidine is prepared by subjecting 2-alkyl-4-amino-5-cyanopyrimidine to reduction, followed by formylation, or by subjecting 2-alkyl-4-amino-5-chloromethylpyrimidine to amination, and subjecting the resulting 2-alkyl-4-amino-5-aminomethylpyrimidine to formylation. The said methods require many steps and the yields are not satisfactory.

The specification of U.S. Pat. No. 2,820,050 discloses the production of a 2-alkyl-4-amino-5-acetyl (or benzoyl) aminomethylpyrimidine by subjecting β-acetyl or benzoylaminopropionitrile to formylation, subjecting the resulting α-sodioformyl-β-acetyl (or benzoyl) amino propionitrile to alkylation, and reacting the resulting compound with an amidine. The said method also gives a poor yield and the desired product is not employable as a starting material as it is for the synthesis of thiamine and its analogues. That is to say, the product of U.S. Pat. No. 2,820,050 must be converted to 2-alkyl-4-amino-5-formylaminomethylpyrimidine through the contact with an alkali solution, followed by reaction with formic acid.

It has now been found by the present inventors that a 2-alkyl-4-amino-5-formylaminomethylpyrimidine represented by the formula

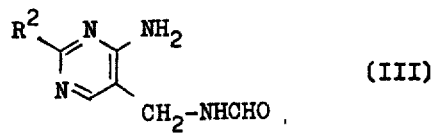

(III)

, wherein $R^2$ stands for an alkyl group, can be obtained in a by far higher yield and through less process steps than those of the known methods. The desired compound is obtained by reacting β-aminopropionitrile with formic ester or carbon monoxide in the presence of a metal alcoholate to produce a metal salt of α-formyl-β-formylaminopropionitrile, then subjecting the thus produced product to alkylation or acylation to obtain a novel compound α-substituted oxymethylene-β-formylaminopropionitrile represented by the formula

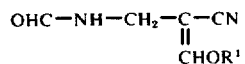

(I)

wherein $R^1$ stands for an alkyl group or an acyl group, followed by reaction of the resulting product that is αsubstituted oxymethylene-β-formylaminopropionitrile with an amidine represented by the formula

(II)

wherein $R^2$ has the same meaning defined above.

In the above general formulas, the alkyl group represented by $R^1$ may be a straight or branched one and is exemplified by a lower alkyl group having from 1 to 4 carbon atoms such as methyl, ethyl, normal-propyl, isopropyl, butyl, isobutyl and secondarybutyl. The acyl group represented by $R^1$ may be one derived from an organic carboxylic acid such as aliphatic, aromatic or aromato-aliphatic mono- or poly-carboxylic acids, and examples of the aliphatic acyl carboxylic acids are those having from 1 to 4 carbon atoms such as acetyl, propionyl and butyryl, examples of the aromatic acyl carboxylic acid, are benzoyl and phthaloyl and an example of the aromato-aliphatic acyl carboxylic acids is phenylacetyl. The acyl group represented by $R^1$ may be one derived from organic mono-substituted carbonic acids such as aliphatic mono substituted carbonic acids having from 2 to 4 carbon atoms such as methoxy carbonyl, ethoxy carbonyl and propoxy carbonyl and an example of the aromatic mono substituted carbonic acid is phenyl carbonyl an an example of aromato-aliphatic mono substituted carbonic acid is benzyloxy carbonyl.

The alkyl group represented by $R^2$ may be a straight or branched one and is exemplified by the same lower alkyl group as $R^1$ mentioned above.

According to the method of the present invention, the reaction is started by formylation of β-aminopropionitrile. The formylation is conducted by reacting β-aminopropionitrile with an ester of formic acid or carbon monoxide in the presence of a metal alcoholate. As the ester of formic acid, any reagents which have been usable for formylation may be employed. The examples of the ester of formic acid are alkyl esters (e.g. methyl ester, ethyl ester, propyl ester or butyl ester), aryl esters (e.g. phenyl ester) and aralkyl esters (e.g. benzyl ester).

As the metals alcoholates, alkali metal (e.g. sodium or potassium) of an aliphatic alcohol (e.g. methanol, ethanol, propanol or butanol) are conveniently used. The examples of the alkali metal aliphatic alcoholates are sodium methylate, sodium ethylate, potassium methylate and potassium ethylate.

Solvents employable in this reaction are exemplified by the afore-mentioned ester of formic acid itself an an inert organic solvent. The examples of the inert organic solvents are ethers (e.g. isopropyl ether, dioxane, diglyme or tetrahydrofuran). Among those, the anhydrous one is preferably employed.

When carbon monoxide is employed, the reaction can be carried out under atmospheric or superatmospheric pressure, and advantageously carried out at a pressure ranging from 10 to 150 kg/cm² gauge, and more preferably from 20 to 80 kg/cm² guage. The reaction temperature is generally from 0° to 150°C, and preferably is from 30° to 100°C.

The amount of the metal alcoholate used is preferably not less than one mole per mole of β-aminopropionitrile, more preferably from 1.0 to 2.0 moles.

The said process gives a metal salt of α-formyl β-formylaminopropionitrile in a high yield.

The thus produced metal salt of α-formyl-β-formylaminopropionitrile is used as a starting material for the next reaction step in a state of the reaction mixture or after purification.

In the second step, the metal salt of α-formyl β-formylaminopropionitrile is subjected to alkylation or acylation. The alkylation is conducted by reacting a metal salt of α-formyl-β-formylaminopropionitrile with an 0-alkylating agent. Examples of the alkylating agent are sulfuric esters (e.g. dimethyl sulfate, diethyl sulfate), alkyl halides (e.g. methyl iodide, methyl bromide) or diazomethane. The acylation is conducted by reacting a metal salt of α-formyl-β-formylaminopropionitrile with an acylating agent. Examples of the acylating agent are aliphatic mono or poly carboxylic acids (e.g. acetic acid, propionic acid, maleic acid, butyric acid), aromatic mono or poly carboxylic acids (e.g. benzoic acid, phthalic acid) and aromato-aliphatic mono or poly carboxylic acids (e.g. phenyl acetic acid), acid halides (e.g. acid chlorides such as acetyl chloride, acid bromides such as acetyl bromide), acid anhydrides (e.g. acetic anhydride), mixed acid anhydrides (e.g. acetic formic anhydride), alkyl carbonic acid halides (e.g. methoxy carbonyl chloride, ethoxy carbonyl chloride).

The reaction may be conducted in the presence of an inert solvent. Examples of the solvent used in the alkylation are alcohols (e.g. methanol, ethanol, propanol), esters (e.g. ethyl acetate, ethyl formate) or ethers (e.g. tetrahydrofuran, dioxane). Examples of the solvent in acylation are esters (e.g. ethyl acetate, ethyl formate) or ethers (e.g. tetrahydrofuran, dioxane).

The alkylation reaction is conducted at a temperature from 0° to 150°C, preferably from 20° to 100°C. And the reaction of the acylation is conducted at a temperature from −10° to 150°C.

When an acid anhydride is employed as an acylating agent, the reaction may preferably be conducted at a temperature from 20° to 150°C, and when acid halide is employed, the reaction may preferably be conducted at a temperature from −10° to 50°C. The amount of alkylating agent used is from 1 to 10 moles per mole of the metal salt of α-formyl-β-formylaminopropionitrile, preferably from 1 to 3 moles. The amount of acylating agent used is from 1 to 10 moles per mole of the metal salt of α-formyl-β-formylaminopropionitrile, preferably from 1 to 3 moles.

The said reaction gives a novel compound, α-alkoxymethylene or acyloxymethylene-β-formylaminopropionitrile represented by the formula (I), in a high yield. The thus produced compound may be subjected to the next reaction as a starting material in a state of the reaction mixture or after purification.

In the third step, α-alkoxymethylene or acyloxymethylene-β-formylaminopropionitrile is reacted with an amidine represented by the formula (II). Examples of the amidines are acetamidine, propioamidine, butyroamidine and valeroamidine. The amount of the amidine used is not less than one mole per mole of the starting material, preferably from 1 to 3 moles. The reaction is conducted at a temperature from 0° to 150°C, more preferably from 20° to 100°C.

The reaction may be conducted in the presence of an inert solvent such as alcohols (e.g. methanol, ethanol, propanol), esters (e.g. ethyl acetate or ethyl formate), ethers (e.g. tetrahydrofuran or dioxane).

Mineral acid salts of amidines may be employed together with metal alcoholates (e.g. sodium ethylate, potassium methylate) or alkali carbonates (e.g. sodium carbonate, potassium carbonate).

Thus, the present method gives 2-alkyl-4-amino-5-formylaminomethylpyrimidine represented by the formula (III) in high yield and using less steps.

The thus produced 2-alkyl-4-amino-5-formylaminomethylpyrimidine can easily be converted to thiamine or its analogues by reacting 2-alkyl-4-amino-5-formylaminomethylpyrimidine with γ-aceto-γ-chloropropyl alcohol and hydrogen sulfide. And the thus produced 2-alkyl-4-amino-5-formylaminomethylpyrimidine can easily be converted to 2-alkyl- 4-amino-5-aminomethylpyrimidine by subjecting it to hydrolysis with a mineral acid (e.g. hydrogen chloride or sulfuric acid) or reaction with an alkali (e.g. sodium hydroxide).

For a further detailed explanation of the invention the following examples are given, wherein the term "part(s)" means "weight part(s)" unless otherwise noted and the relationship between "part(s)" and "part(s) by volume" corresponds to that between "gram(s)" and "milliliter(s)".

EXAMPLE 1

To 59.5 parts of sodium methylate is added 300 parts by volume of methyl formate and the mixture is cooled down to 5°C. The mixture is dissolved in 70 parts of β-aminopropionitrile. The solution is put into an autoclave with a capacity of 1,000 parts by volume. Into the solution is introduced carbon monoxide at 30 kg/cm²G, and the reaction is continued at 60°C until the pressure no longer drops.

After the reaction is completed, the precipitated crystals are recovered by filtration and washed with a small amount of methyl formate and then dried, whereby 132 parts of α-sodioformyl-β-formylaminopropionitrile melting at 191°C with decomposition is obtained as crystals. Nuclear magnetic resonance spectrum (D₂O, 60 Mc);

$\delta$ =8.0  -8.1(CHO),  $\delta$ =8.5(HCOONa),  $\delta$ =3.3(CH₃O⁻).

The said NMR spectrum shows that the purity of the product is 90 %. Yield: 80 %.

In 400 parts by volume of ethyl formate is dissolved 35 parts of β-aminopropionitrile. To the solution is added 100 parts of a methanol solution which includes 32 parts of sodium methylate. The mixture is put into an autoclave with a capacity of 1,000 parts by volume. Into the mixture is introduced carbon monoxide at 50kg/cm²G at 70°C for 3 hours. After the reaction, the mixture is cooled at 25°C. The solvent is removed and the crystals are recovered by filtration and dried, whereby 77 parts of α-sodioformyl-β-formylaminopropionitrile is obtained as crude crystals. Purity; 90 %. Yield: 94 %. Melting point; 190°C.

In 300 parts by volume of methyl formate is dissolved 70 parts of β-aminopropionitrile. To the solution is added 270 parts of a methanolic solution containing 97.2 parts of sodium methylate. To the mixture is introduced carbon monoxide at 30 kg/cm²G at 70°C under stirring. After 2 hours of the reaction, the pressure is brought up to 80 kg/cm²G and kept at this pressure for 4 hours. After completion of the reaction, the mixture is cooled at 25°C and distilled, to remove the solvent. The obtained crystals are recovered by filtration and dried, whereby 191.6 parts of α-sodioformyl-β-formylaminopropionitrile is obtained as crude crystals. Purity: 71.4 %. Yield: 92.5%.

In 300 parts by volume of methanol is dissolved 25.3 parts of metal sodium to prepare a methanol solution of sodium methylate. The thus prepared methanol solution of sodium methylate is concentrated under reduced pressure to dryness. And, to the thus obtained sodium methylate is added 300 parts by volume of methyl formate and the mixture is cooled at 5°C. After cooling, to the mixture is added 70 parts of β-aminopropionitrile. Into the mixture is introduced carbon monoxide at 30 kg/cm²G under stirring at 70°C for 4 hours. After standing overnight, the reaction mixture is subjected to distillation to remove the methyl formate.

To the residue of α-sodioformyl-β-formylaminopropionitrile is added 300 parts by volume of tetrahydrofuran and 138 parts of dimethyl sulfate. The mixture is reacted under stirring at 70°C for 5 hours. After completion of the reaction, the mixture is cooled at 25°C. The precipitated sodium methyl sulfate is removed and the filtrate is concentrated and kept standing overnight, whereby 135 parts of α-methoxymethylene-β-formylaminopropionitrile is obtained as crystals.

The thus obtained crystals are subjected to distillation at 185° to 190°C under pressure of 2 mmHg and then to recrystallization from ether-ethanol, whereby crystals of α-methoxymethylene-βformylaminopropionitrile are obtained. Melting point: 84° to 86°C. Yield: 98 g. (70 %). UV absorption λ max($H_2O$); 230 m$\mu$. $E^{1\%}_{1cm}$ = 1102

To 100 parts by volume of ethanol is dissolved 25.6 parts of α-methoxymethylene-β-formylaminopropionitrile to prepare an ethanolic solution of α-methoxymethylene-β-formylaminopropionitrile.

To 75 parts by volume of ethanol is added 32.5 parts of acetamidine hydrochloride and 18.7 parts of sodium methylate. The precipitated sodium chloride is separated by filtration to give an acetamidine solution.

The α-methoxymethylene-β-formylaminopropionitrile solution and the acetamidine solution are combined. The mixture is reacted at 25°C for 10 minutes. The reaction mixture is subjected to concentration at not higher than 40°C to give crystals. The produced crystals are washed with 50 parts by volume of ethanol, whereby 24.8 parts of 2-methyl-4-amino-5-formylaminomethylpyrimidine is obtained as crystals (Purity: 93 %). The ethanol washing is concentrated to give 16 parts of 2-methyl-4-amino-5-formylaminomethylpyrimidine as crystals (Purity: 47.5 %).

The yield of the above procedure is 100 %. Melting point of the produced crystals recrystallized from ethanol is 225°C.

UV absorption
λ max ($H_2O$) 235 m$\mu$$E_{1cm}^{1\%}$ = 480 λ max ($H_2O$) 267 m$\mu$ $E_{1cm}^{1\%}$ = 317

EXAMPLE 2

To 59.5 parts of sodium methylate is added 300 parts by volume of tetrahydrofuran, and the mixture is cooled at −5°C and then to the mixture is added dropwise 70 parts of β-aminopropionitrile. Into the mixture is introduced carbon monoxide at 50 kg/cm²G at 70°C for 4 hours to allow the reaction to take place. After completion of the reaction, the solvent is removed and the crystals are recovered by filtration and washed with tetrahydrofuran, whereby 116 parts of α-sodioformylβ-formylaminopropionitrile is obtained. Melting point: 178°C(decomp.) Purity: 79 %. Yield: 62 %.

To crystals of 34 parts (Purity: 91 %) of α-sodioformyl-β-formylaminopropionitrile is added 250 parts by volume of tetrahydrofuran and 25 parts of acetic acid anhydride. The mixture is reacted at 70°C for 5 hours. The precipitated sodium acetate is removed by filtration and by washing with 35.5 parts by volume of tetrahydrofuran. The filtrate is concentrated, whereby 35.5 parts of an oily substance is obtained.
NMR($D_2O$, 60 Mc):
$\delta$ =2.3($CH_3$), $\delta$ =3.9($CH_2$), $\delta$ =6.5(CH),
$\delta$ =8.2(CHO)

The product is identical with α-acetoxymethylene-βformylaminopropionitrile by the above NMR.
UV absorption: λ max($H_2O$): 256 m$\mu$.

In 20 parts by volume of ethanol is dissolved 5 parts of α-acetoxymethylene-β-formylaminopropionitrile. To the mixture is added an ethanol solution of acetamidine which is prepared from 3.5 parts of acetamidine hydrochloride and 2.0 parts of sodium methylate. The mixture is reacted at 60°C for 30 minutes. Ethanol is removed from the reaction mixture by distillation, whereby 3 parts of 2-methyl-4-amino-5-formylaminomethylpyrimidine is obtained as crystals (Yield: 60 %).

EXAMPLE 3

300 Parts by volume of methyl formate, 59.5 parts of sodium methylate and 70 parts of β-aminopropionitrile are mixed together. The mixture is put into a sealed vessel with a capacity of 1,000 parts by volume and reacted at 70°C for 4 hours. After completion of the reaction, the mixture is cooled at 25°C and is treated in the same manner as described in Example 1, whereby 120 parts of α-sodioformyl-β-formylaminopropionitrile (Purity: 80 %) is obtained. In 250 parts by volume of tetrahydrofuran is dissolved 41 parts of α-sodioformyl-β-formylaminopropionitrile obtained in the manner similar to above procedure. To the mixture is added 31.5 parts of dimethyl sulfate and the mixture is refluxed at 70°C for 5 hours. After completion of the reaction, the reaction mixture is treated in the same manner as in Example 1, whereby 29.5 parts of α-methoxymethylene-β-formylaminopropionitrile is obtained. (Yield: 95 %).

In 50 parts by volume of ethanol is dissolved 14 parts of α-methoxymethylene-β-formylaminopropionitrile. To the solution is added 100 parts by volume of an ethanol solution containing 17 parts of propioamidine. The mixture is reacted at 30°C for 0.5 hour. After the reaction, ethanol is distilled off and the residue is cooled at 25°C, whereby 18 parts of 2-ethyl-4-amino-5-formylaminomethylpyrimidine is obtained as crystals. (Yield: 100 %). Recrystallization of the crystals from benzene-ethanol mixture gives colorless crystals melting at 185°C.

What we claim is:
1. A method for the production of a 2-alkyl-4-amino-5-formylaminomethyl pyrimidine of the formula:

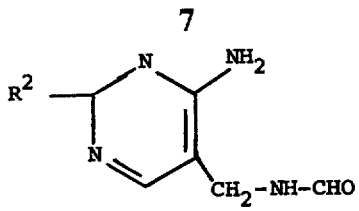

wherein $R^2$ is an alkyl group having 1 to 4 carbon atoms which comprises:
a. reacting β-aminopropionitrile with an alkyl formate having 2 to 5 carbon atoms, and carbon monoxide in the presence of $C_{1-4}$ alkyl alcoholate of an alkali metal at a temperature varying from 0°C to 150°C to obtain the alkali metal salt of α-formyl-β-formylamino propionitrile,
b. reacting said alkali metal salt of α-formyl-β-formylaminopropionitrile with $C_1$-$C_4$ alkyl esters of sulfuric acid, an alkyl halide or diazomethane at a temperature ranging from 0°C to 150°C to obtain an α-substituted oxymethylene-α-formyl aminopropionitrile of the formula:

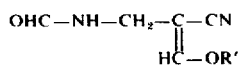

wherein R' is alkyl of 1 to 4 carbon atoms, and
c. reacting said α-substituted oxymethylene-β-formylaminopropionitrile with an amidine of the formula

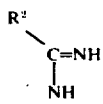

wherein $R^2$ is as defined above, or a mineral acid salt of said amidine at a temperature varying from about 0°C to 150°C to obtain said 2-alkyl-4-amino-5-formylaminomethyl) pyrimidine.

2. A method according to claim 1 in which in said step (c) the said α-substituted oxymethylene-β-formylamino-propionitrile is α-methoxymethylene-β-formylamino propionitrile and said mineral acid salt of amidine is acetamidine hydrochloride to obtain 2-methyl-4-amino-5-formylamino methyl pyrimidine said reaction being conducted at a temperature of about 25°C.

3. A method according to claim 1 in which in said step (c) the said α-substituted oxymethylene-μ-formylamino propionitrile is α-acetoxymethylene-β-formylamino propionitrile and said amidine is acetamidine to obtain 2-methyl-4-amino-5-formylamino methylpyrimidine said reaction being conducted at a temperature of about 50°C.

4. A method according to claim 1 in which in said step (c) the said α-substituted oxymethylene-β-formylamino propionitrile is α-methoxymethylene-β-formylamino propionitrile and said amidine is propionamidine to obtain 2-ehtyl-4-amino-5-formylamino methyl pyrimidine, the reaction being effected at a temperature of about 30°C.

5. A method according to claim 1 in which in said step (b) the said alkali metal salt of α-formyl-β-formyl aminopropionitrile is α-sodio formylβ-formylamino propionitrile and said $C_1$-$C_4$ alkyl ester of sulfuric acid is dimethyl sulfate to obtain α-methoxy-methylene-β-formylamino propionitrile, the reaction being conducted at a temperature of about 70°C.

6. A method according to claim 1 in which in said step (a) β-amino-propionitrile is reacted with methyl formate and carbon monoxide in the presence of sodium methylate at a temperature of 60°C to obtain α-sodiomformyl-β-formylamino propionitrile.

7. A method according to claim 1 in which in said step (a) β-amino-propionitrile is reacted with methyl formate and carbon monoxide in the presence of sodium methylate at a temperature of 70°C to obtain α-sodioformyl-β-formylamino propionitrile.

8. A method according to claim 1 in which in said step (a) β-amino-propionitrile is reacted with ethyl formate and carbon monoxide in the presence of sodium methylate at a temperature of 70°C to obtain α-sodioformyl-β-formylamino propionitrile.

* * * * *